US006885013B2

(12) United States Patent
Loda

(10) Patent No.: US 6,885,013 B2
(45) Date of Patent: Apr. 26, 2005

(54) SYSTEM FOR, AND METHOD OF, IRRADIATING ARTICLES

(75) Inventor: Gary K. Loda, Pleasanton, CA (US)

(73) Assignee: Surebeam Corporation, San Diego, CA (US)

( * ) Notice: Subject to any disclaimer, the term of this patent is extended or adjusted under 35 U.S.C. 154(b) by 0 days.

(21) Appl. No.: 10/428,661

(22) Filed: May 2, 2003

(65) Prior Publication Data

US 2004/0217301 A1 Nov. 4, 2004

(51) Int. Cl.[7] .............................. A61N 5/00; G21G 5/00

(52) U.S. Cl. .................................................. 250/492.1

(58) Field of Search .......................... 250/492.1, 432 R, 250/433, 435, 492.3, 492.2

(56) References Cited

U.S. PATENT DOCUMENTS 6,528,800 B1 * 3/2003 Dzwierzynski et al. . 250/432 R
6,653,641 B1 * 11/2003 Lyons et al. ............. 250/492.2
6,683,319 B1 * 1/2004 Koenck et al. .......... 250/492.3
2002/0179853 A1 * 12/2002 Olson ...................... 250/492.1
2003/0221722 A1 * 12/2003 Hogsden et al. ............ 137/207

* cited by examiner

*Primary Examiner*—Jack Berman
*Assistant Examiner*—Johnnie L Smith, II
(74) *Attorney, Agent, or Firm*—Peter K. Hahn; David E. Heisey; Luce, Forward, Hamilton and Scripps, LLP

(57) ABSTRACT

Articles having irregular characteristics such as an irregular geometrical configuration or an irregular density are disposed in a container which is moved in a first direction past a radiation source. Radiation from the source is directed toward the articles in the container in a second direction substantially perpendicular to the first direction. The radiation energy passing from the source to the articles at different positions in the articles is absorbed in accordance with the irregularities in the characteristics of the articles at the different positions to maintain the radiant energy at the different positions in the articles within particular limits. For irregularities of geometrical configuration or density in the articles, the absorption may be provided during the movement of the container in the first direction with a fixture which has a geometrical configuration or density constituting the difference at every position between a substantially constant value and the geometrical configuration or density of the articles at this position. The fixture is disposed inside the container. The fixture may be a fluid such as water.

56 Claims, 4 Drawing Sheets

SYSTEM FOR, AND METHOD OF, IRRADIATING ARTICLES

This invention relates to systems for, and methods of, irradiating products, including food products, to make them safe to use or eat. The invention particularly relates to systems for, and methods of, providing the irradiation within particular limits regardless of irregularities in the characteristics, including irregularities in the geometric shape, of the products including the food products.

BACKGROUND OF A PREFERRED EMBODIMENT OF THE INVENTION

It has been known for some time that drugs and medical instruments and implements have to be irradiated so that they will not cause patients to become ill from harmful bacteria when they are applied to the patients. Systems have accordingly been provided for irradiating drugs and medical instruments and implements. The drugs and the medical instruments and implements have then been stored in sterilized packages until they have been ready to be used.

In recent years, it has been discovered that foods can carry harmful bacteria if they are not processed properly or, even if they are processed properly, that the foods can harbor and foster the proliferation of such harmful bacteria if they are not stored properly or retained under proper environmental conditions such as temperature. Some of the harmful bacteria can even be deadly.

For example, harmful bacteria have been discovered in recent years in hamburgers prepared by one of the large hamburger chains. Such harmful bacteria have caused a number of purchasers of hamburgers at stores in the chain to become sick. As a result of this incident and several other similar incidents, it is now recommended that hamburgers should be cooked to a well done state rather than a medium rare or rare state. Similarly, harmful bacteria have been found to exist in many chickens that are sold to the public. As a result of a number of incidents which have recently occurred, it is now recommended that all chickens should be cooked until no blood is visible in the cooked chickens.

To prevent incidents such as discussed in the previous paragraphs from occurring, various industries have now started to irradiate foods before the goods are sold to the public. This is true, for example, of hamburgers and chickens. It is also true of fruits, particularly fruits which are imported into the United States from foreign countries.

In previous years, gamma rays have generally been the preferred medium for irradiating various articles. The gamma rays have been obtained from a suitable material such as cobalt and have been directed to the articles to be irradiated. The use of gamma rays has had certain disadvantages. One disadvantage is that irradiation by gamma rays is slow. Another disadvantage is that irradiation by gamma rays is not precise. This results in part from the fact that the strength of the source (e.g. cobalt) of the gamma rays decreases over a period of time and that the gamma rays cannot be directed in a sharp beam to the articles to be irradiated. This prevents all of the gamma rays from being useful in irradiating the articles.

In recent years, electron beams have been directed to articles to irradiate the articles. Electron beams have certain advantages over the use of gamma rays to irradiate articles. One advantage is that irradiation by electron beams is fast. For example, a hamburger patty having a square cross section can be instantaneously irradiated by a passage of an electron beam of a particular intensity through the hamburger patty. Another advantage is that irradiation by an electron beam is relatively precise because the strength of the electron beam remains substantially constant even when the electron beam continues to be generated over a long period of time.

X-rays have also been used to irradiate articles. The x-rays may be formed from electron beams. An advantage in irradiating articles with x-rays is that the articles can be relatively thick. For example, x-rays can irradiate articles which are thicker than the articles which are irradiated by electrons.

A problem has occurred in the past whether the irradiation has been provided by gamma rays, electrons or x-rays. This has occurred when the articles have had irregular characteristics such as irregular geometrical configurations. For example, a meat chub is generally circular in vertical section. This has caused the thickness of the chub to be different at every position in a vertical direction in the cylindrical shape of the chub. These differences in thickness have affected the radiation which the chubs have received at the different positions.

The radiation received at every position in an article should be within particular minimum and maximum limits. If the radiation received at any position within the article is below the particular minimum limit, harmful bacteria in the articles at that position may not be destroyed. If the radiation received at any position in the article is above the particular maximum limit, the quality or organoleptic characteristics of the article may be negatively affected. It is difficult to maintain the radiation in the articles within the particular minimum and maximum limits when the article has irregularities in the characteristics at the different positions such as irregularities in the geometric configuration of the article. For example, a chub having a cylindrical configuration may be considered to have irregularities in characteristics because the vertical dimensions of the chub at the progressive positions of the chub in the horizontal radial direction are different. Irregularities in characteristics at different positions in an article may also result from irregularities in density at the different positions in the article.

Ethafoam and other equivalent materials have been disposed between the source of radiation and an article, particularly when the article is a drug or a medical instrument, to reduce the dosage applied to the article within particular minimum and maximum limits. However, the reduction in the radiation dosage of the article is not provided at different positions in the article in accordance with irregularities in the characteristics of the article at the different positions.

In co-pending application Ser. No. 09/872,441 (SUREB-56121), filed by DENNIS G. OLSON for SYSTEM FOR, AND METHOD OF, IRRADIATING ARTICLES and assigned of record to the assignee of record of this application, an article has irregular characteristics such as an irregular geometrical configuration. Radiation from a source is directed in a particular direction toward the article. The radiation energy from the source to the article at different positions in the article is absorbed in accordance with the irregularities in the characteristics of the article at the different positions to maintain the radiant energy at the different positions in the article within particular limits.

For irregularities of geometrical configuration in the article in Ser. No. 09/872,441 (SUREB-56121), the absorption may be provided by a fixture having a geometrical configuration which constitutes the difference at every position between a substantially constant value and the geometrical configuration of the article at this position. The absorption is provided by conveying the article and the fixture past the radiation source in a direction substantially perpendicular to the direction of the radiation from the source.

In co-pending application (SUREB-57333) filed by John Thomas Allen, George Sullivan, Jr., and Colin Brian Williams, the articles are disposed in a container and the fixtures are disposed externally relative to the container. For irregularities of geometrical configuration or density in the article, the absorption may be provided by a fixture having a geometrical configuration or density which constitutes the difference at every position between a substantially constant value and the geometrical configuration or density of the article at this position.

BRIEF DESCRIPTION OF A PREFERRED EMBODIMENT OF THE INVENTION

In a preferred embodiment of the invention, articles having irregular characteristics such as an irregular geometrical configuration or an irregular density are disposed in a container which is moved in a first direction past a radiation source. Radiation from the source is directed toward the articles in the container in a second direction substantially perpendicular to the first direction. The radiation energy passing from the source to the articles at different positions in the articles is absorbed in accordance with the irregularities in the characteristics of the articles at the different positions to maintain the radiant energy at the different positions in the articles within particular limits.

For irregularities of a geometrical configuration or a density in the articles, the absorption may be provided by a fixture having a geometrical configuration or density which constitutes the difference at every position between a substantially constant value and the geometrical configuration or density of the articles at this position. The absorption may be provided during the movement of the container in the first direction with a fixture which has a geometric configuration or a density constituting the differences at every position between a substantially constant value and the respective one of the geometrical configuration or density of the articles at this position. The fixture is disposed within the container. The fixture may be a fluid such as water.

DETAILED DESCRIPTION OF THE PREFERRED EMBODIMENTS

Figure 1:
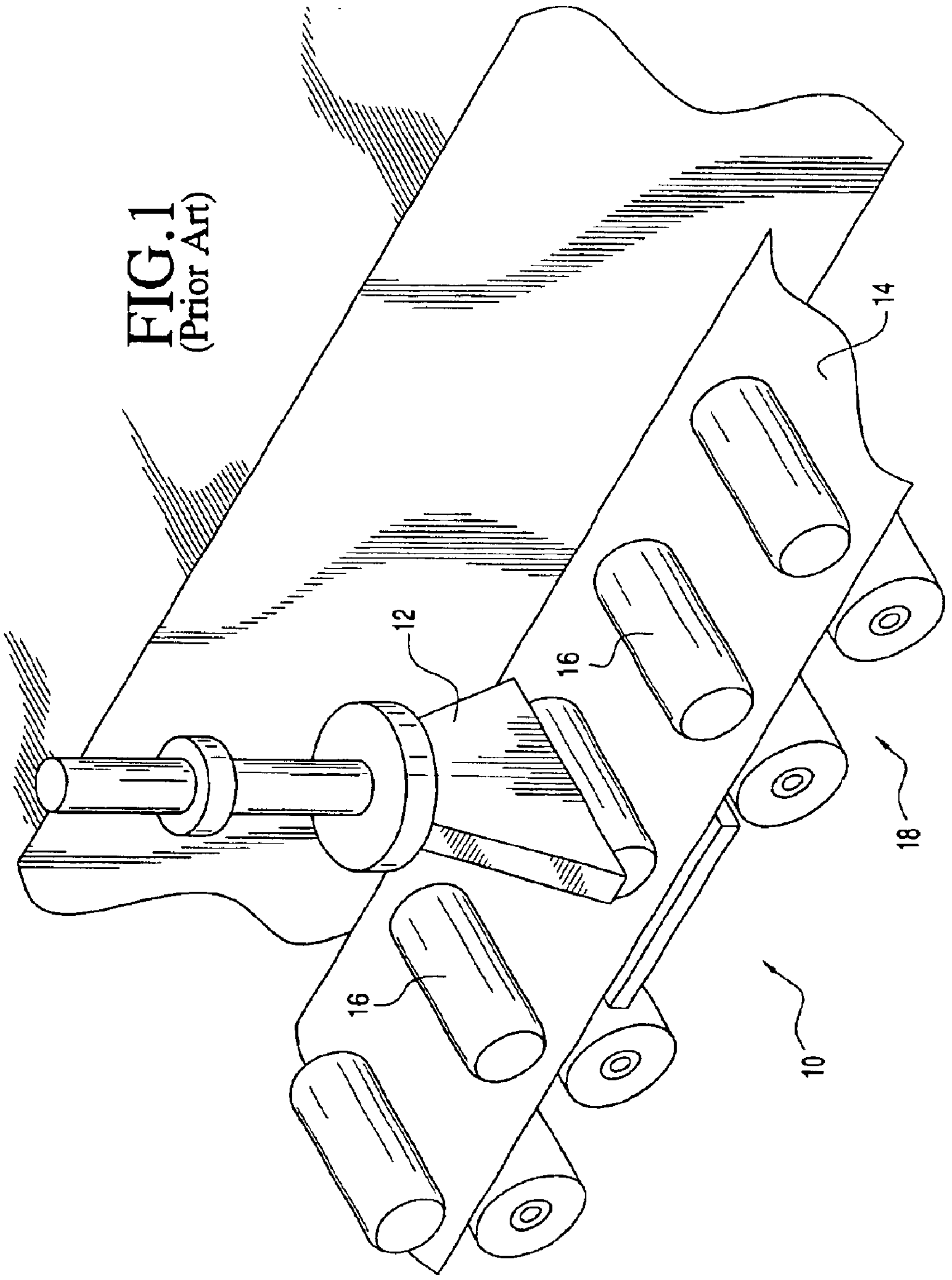
FIG.1 (Prior Art)
FIG. 1 is a simplified perspective view showing a system of the prior art for conveying an article past a source of radiation to irradiate the article.

FIG. 1 is a simplified diagram of an irradiation system, generally indicated at 10, of the prior art for conveying an article past a source of radiation 12. For example, the conveyor system may be constructed as shown and described in U.S. Pat. No. 5,396,074 issued on Mar. 7, 1995, and assigned of record to the assignee of record of this application. The conveyor system 10 includes a conveyor 14 for moving articles 16 past the radiation source 12 for irradiation of the articles by the source. The articles may be moved past the radiation source at a substantially constant speed within particular limits. The distance between successive articles on the conveyor 14 may be maintained at a minimal value within particular limits. The articles 16 may be irradiated with gamma rays, electrons or x-rays or any other type of radiation without departing from the scope of the invention.

The articles 16 may have irregular characteristics at different positions. These irregular characteristics may include irregularities in geometrical configuration or in density or in a combination of irregularities in geometrical configuration and density. For example, the articles 12 may constitute chubs having a cylindrical shape. The radiation from the source may pass through each chub in a vertical direction corresponding to the circular cross section of the chub.

Figure 2:
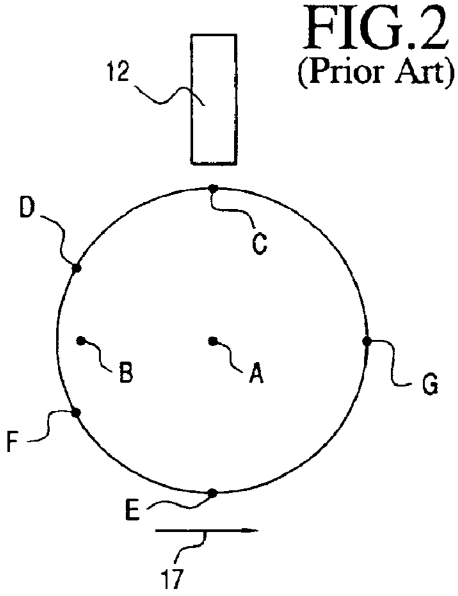
FIG.2 (Prior Art)
FIG. 2 is a simplified view illustrating how a system of the prior art irradiates an article such as a chub having a circular configuration in a vertical section.

FIG. 2 illustrates a plan view of the article 16 when the article is a chub. The chub moves in a direction 17 past the accelerator 12. The direction is perpendicular to the direction of the radiation from the accelerator 12. As will be seen, the irradiation provided at a position A in the chub 16 is different from the irradiation provided at a position B in the chub even though the positions A and B are at the same distance in FIG. 2 from the accelerator 12 when the positions A and B are aligned with the accelerator. This results from the fact that the radiation has to pass through the chub 16 between the positions C and A on the one hand when the chub moves at positions C and A past the accelerator. On the other hand, the radiation has to pass only through the distances between D and B as the chub moves at the positions D and B past the accelerator.

The irradiation of the chub at the position A is accordingly different than the irradiation of the article at the position B. This may cause the chub to be under-radiated at some positions in the chub and to be over-radiated at other positions in the chub. Under radiating in the chub is undesirable because harmful bacteria in the chub are not killed.

Over-radiating is undesirable because the quality or organoleptic characteristics of the chub may be negatively affected. It is accordingly desirable to radiate the chub within particular minimum and maximum limits. This causes harmful bacteria to be killed and the quality or organoleptic characteristics of the chub to be retained.

Opposite sides of the chub 14 may be irradiated by rotating the chub through 180ÿ and then subjecting the chub to radiation a second time or by simultaneously irradiating the chub from opposite sides of the chub. However, irradiating the chub from opposite sides of the chub does not have any effect on the dissimilarities of the radiation at the positions A and B. The reason is that the distance between E and A is the same as the distance between C and A and the distance between F and B is the same as the distance between D and B. As will be appreciated, the positions between C, A and E define a straight line and the positions between D, B and F also define a straight line. The direction between the positions C and E, and between the positions D and F, is substantially parallel to the direction of the radiation from the accelerator 12.

Although the discussion in the previous paragraphs has related to irregularities in the geometrical configuration of the articles, the discussion relates equally as well to irregularities in the density characteristics of the articles or to a combination of irregularities in the geometrical configuration and in the density of the articles.

Co-pending application Ser. No. 09/710,730 filed in the U.S. Patent Office on Nov. 10, 2000 and assigned of record to the assignee of record of this application discloses and claims a member disposed between a radiation source and an article. The member absorbs the radiation from the source, when the radiation is above the preferred maximum limit, so that the radiation passing through the source to the article will be within the preferred maximum and minimum limits in the article. However, the member is stationary.

The invention disclosed and claimed in application Ser. No. 09/872,441 assigned of record to the assignee of record of this application provides a simple but ingenious solution to the problems discussed above. In accordance with one embodiment shown in FIG. 3, the article 14 is disposed in a fixture, generally indicated at 20, which may be a plastic or a metal such as aluminum, steel, or any other material having similar characteristics, in response to radiation from the accelerator 12, to those of the article 16. The geometrical configuration of the fixture 20 in a planar direction corresponding to the direction of the radiation from the accelerator 12 complements the geometrical configuration of the article 14 such that the combined or composite configuration of the fixture 20 and the article 14 is essentially a square in section. The article 14 does not have to be disposed snugly within the fixture 20. The fixture 20 is movable with the article 14 past the accelerator 12. It will be appreciated that the same principles and solutions discussed above apply equally as well to irregularities in the density of articles at different positions in the articles and to irregularities constituting combinations in the irregularities in the geometrical configurations and densities in the articles.

In other words, the dimension of the composite of the article 14 and the fixture 20 in the direction of the radiation from the accelerator source 12 in application Ser. No. 09/872,441 is substantially the same at every position in the direction of the radiation from the accelerator 12 when the composite is moved on the conveyor past the radiation in a direction substantially perpendicular to the direction of the radiation from the source. In this way, the radiation dosage of the article 14 at the position B is the same within the maximum and minimum limits as the radiation dosage of the article at the position A. This is also true for every position along the line between B and A and at every position along the extension of this line between A and E.

The fixture 20 in application Ser. No. 09/872,441 has at the progressive positions characteristics constituting the difference between substantially constant characteristics and the characteristic of the article at the progressive positions. These characteristics may include geometrical configurations or densities of the article at the progressive positions. The fixture 20 is disposed relative to the article 16 to provide the substantially constant characteristics for the combination of the article and the fixture at the progressive positions in the direction substantially perpendicular to the direction of the radiation from the accelerator 12. When there are irregularities in the geometric shape of the article, the fixture is disposed relative to the article to provide a substantially constant geometric shape for the combination of the article and the fixture at the progressive positions in the article. The same principles apply to irregularities in the density of the article as to irregularities in the geometrical configuration of the articles.

Thus, the radiant energy passing from the source 12 to the article 16 at the different positions in application Ser. No. 09/872,441 is absorbed in accordance with the irregularities of the article at the different positions so as to maintain the radiation dosage at the different positions in the article within the particular limits. Applicant's assignee provides for the deposition of the radiant dosage from the source within the particular limits at the different positions in the article regardless of the irregularities in the characteristics of the article at the different positions. As will be seen, applicant's assignee compensates for the irregularities in the characteristics of the article at the different positions in the article to provide a substantial uniformity in the radiation dose at the different positions in the article within the particular limits.

In application Ser. No. 09/872,441, applicant's assignee also accomplishes the results specified in the previous paragraph (a) by providing a fixture having irregular characteristics, such as an irregular geometric shape or density, at progressive positions to compensate for the differences in the irregularities of the characteristics, such as the irregularities in the geometric shape or density of the article, at the progressive positions and (b) by disposing the fixture relative to the article to provide the combination of the article and the fixture with the compensating characteristics at the progressive positions in response to the radiation.

The fixture 20 in application Ser. No. 09/872,441 has characteristics of receiving at the progressive positions different amounts of radiation per unit of distance of travel of the radiation through the fixture. The different amounts of radiation per unit of distance for the fixture 20 correspond to the different amounts of the radiation per unit of distance for the article to maintain, within the particular limits at the progressive positions, the radiation dosage received by the article per unit of travel of the radiation through the article.

Figure 3:
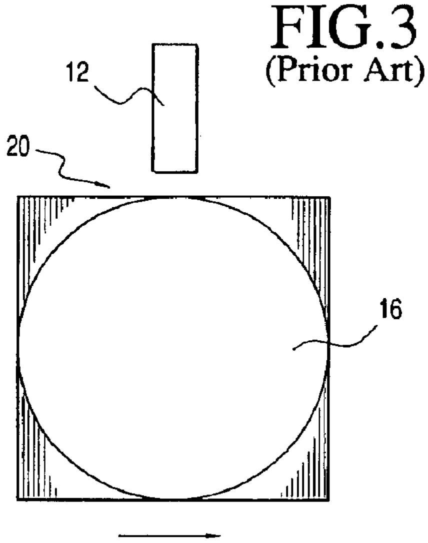
FIG.3 (Prior Art)
FIG. 3 is a simplified view indicating how a system of the prior art provides for an irradiation of an article such as a chub regardless of irregularities in the characteristics, such as irregularities in the geometrical configuration of the article, to provide for an irradiation of the article at the different positions in the article with a dosage within particular minimum and maximum limits.
Figure 4:
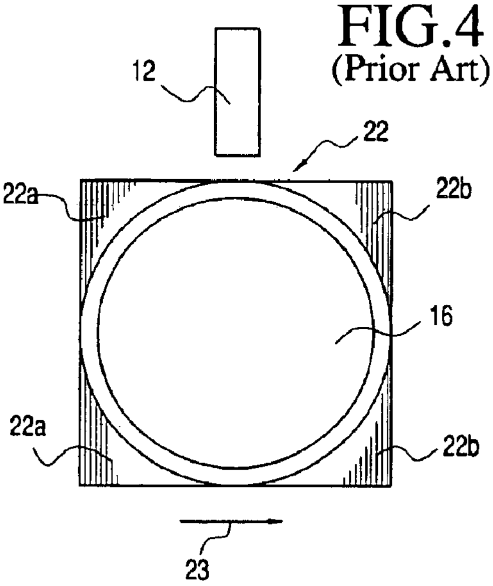
FIG.4 (Prior Art)
FIG. 4 is a simplified view showing how the apparatus of the prior art may include a fixture movable with the article past the radiation from the source to provide for an irradiation of the article at different positions of the article with an intensity within the particular minimum and maximum limits.

FIG. 4 illustrates a fixture, generally indicated at 22, which constitutes a modification of the fixture 20 shown in FIG. 3. The fixture 22 may constitute fixtures 22*a* on one side of the article 14 in the direction of the radiation from the accelerator 12 and fixtures 22*b* on the other side of the article in the direction of the radiation from the accelerator.

When the irregularities on the opposite sides of the article 14 in co-pending application Ser. No. 09/872,441 are symmetrical, the irregularities in the fixtures 22*a* and 22*b* are also preferably symmetrical. However, if the irregularities in the geometrical shape on the opposite sides of the article 16 are not symmetrical, the irregularities in the geometric shape of the fixtures 22*a* on the opposite sides of the article are correspondingly not symmetrical and the irregularities in the geometric shape of the fixtures 22*b* on the opposite sides of the article are correspondingly not similar. The same principles apply to irregularities in the density of the articles at the different positions in the articles as to irregularities in the geometrical shape of the articles at the different positions in the articles.

As will be seen in FIG. 4, the irregularities in the geometrical shape or density of the fixtures 22*a* and 22*b* in co-pending application Ser. No. 09/872,441 extend into the irregularities of the geometrical shape or density of the article 14. The fixtures 22*a* and 22*b* are movable with the article 14 past the radiation from the accelerator 12, preferably in a direction substantially perpendicular to the direction of the radiation from the accelerator 12. This is indicated by an arrow 23.

Figure 5:
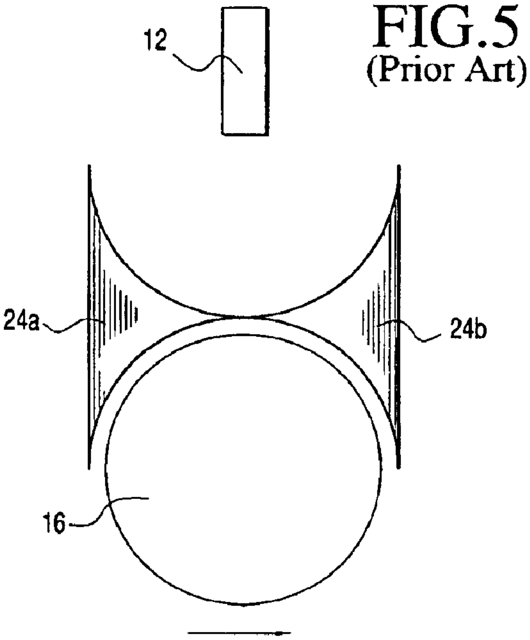
FIG.5 (Prior Art)
FIG. 5 is a simplified view indicating a modification of the prior art fixture shown in FIG. 4.

In FIG. 5, the fixtures 22 and 22*b* in co-pending application Ser. No. 09/872,441 are combined to produce single fixtures 24*a* and 24*b*. The fixture 24*a* has irregularities in its geometrical shape or density corresponding to a combination of the irregularities in the fixtures 22*a* in FIG. 4 at progressive positions substantially perpendicular to the direction of the radiation from the accelerator 12. In like manner, the fixture 24*b* has irregularities in its geometrical shape or density corresponding to a combination of irregularities in the fixture 22*b* in FIG. 4 at progressive positions substantially perpendicular to the direction of the radiation from the accelerator 12. The fixtures 24*a* and 24*b* are movable with the article 14 past the accelerator 12. The fixtures 24*a* and 24*b* attenuate the radiation from the accelerator 12 in a manner similar to the combination of the attenuations provided by the fixtures 22*a* and 22*b* in FIG. 4. The fixtures 24*a* and 24*b* extend into the irregular shape of the article 14.

In the embodiments shown in FIGS. 3–5, the fixtures (e.g. the fixtures 22*a* and 22*b* in FIG. 4) extend into the space between the upper and lower boundaries of the article 15. For example, the upper areas of the fixtures 22*a* and 22*b* extend into the space below the top of the articles 16 in FIG. 4. In like manner, the lower areas of the fixtures 22*a* and 22*b* in FIG. 4 extend into the space above the portion of the articles 116 in FIG. 4. This prevents the article 16 from being boxed. As will be appreciated, it is desirable to irradiate the articles 16 after they have been boxed. This is particularly true when a plurality of articles 16 are disposed in a single box or container.

Figure 6:
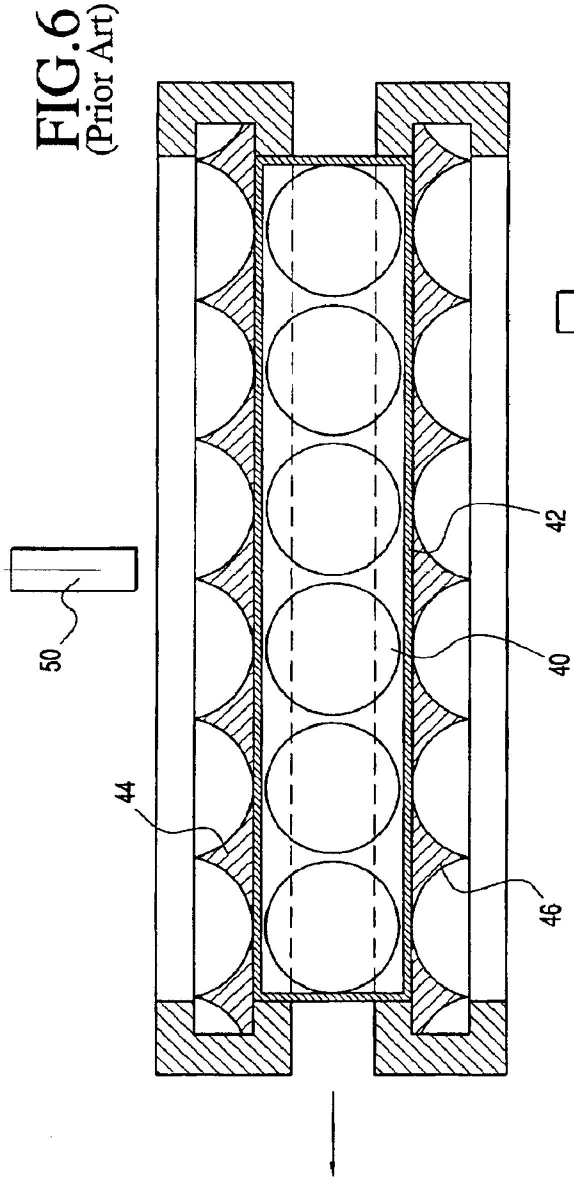
FIG.6 (Prior Art)
FIG. 6 is a simplified view indicating a prior art system in which articles having irregular characteristics are disposed in a container and in which a fixture external to the container is moved with the container past the radiation source to provide for articles within the container to be irradiated within the particular limits of maximum and minimum dosage at different positions in the articles.

FIG. 6 illustrates an arrangement which is disclosed and claimed in co-pending application Ser. No. 09/912,576 and in which a plurality of articles 40 are disposed in a box or container 42. For example, the articles 40 may be chubs. Although the words "box" or "container" are used, the words are intended, individually and in combination in the claims, to indicate any type of housing for the articles. The articles 40 are preferably all of the same configuration although articles 40 of different configurations may be disposed in the same box. Fixtures 44 are disposed above the top of the box or container 42 and fixtures 46 are disposed below the bottom of the box or container 42.

The fixtures 44 and 46 disclosed and claimed in co-pending application Ser. No. 09/912,576 may have the same configuration when the articles 40 in the box or container 42 have the same configuration and when the irregularities at the upper end of the articles 40 are symmetrical with the irregularities at the lower ends of the articles. For example, the articles 40 in the box or container 42 may constitute chubs having a cylindrical configuration. When the upper ends of the articles 40 in the box or container 42 are not symmetrical with the lower ends of the articles, the fixtures 42 above the top of the box or container 42 may have a different configuration than the fixtures 44 below the lower end of the box or container 42.

As will be seen in FIG. 6, the fixtures 44 and 46 disclosed and claimed in application Ser. No. 09/912,576 can be considered, as a practical matter, to be inverted relative to the disposition of the fixture in FIGS. 3–6 so as to be disposed exteriorly of the box or container 42. This allows the fixtures 44 to be closely spaced relative to the top of the box or container 42 and the fixtures 46 to be closely spaced relative to the bottom of the box or container 42. The fixtures 44 and 46 may be moved synchronously with the box or container 42 past a radiation source 50 corresponding to the radiation source 12 in FIGS. 3–5.

Figure 7:
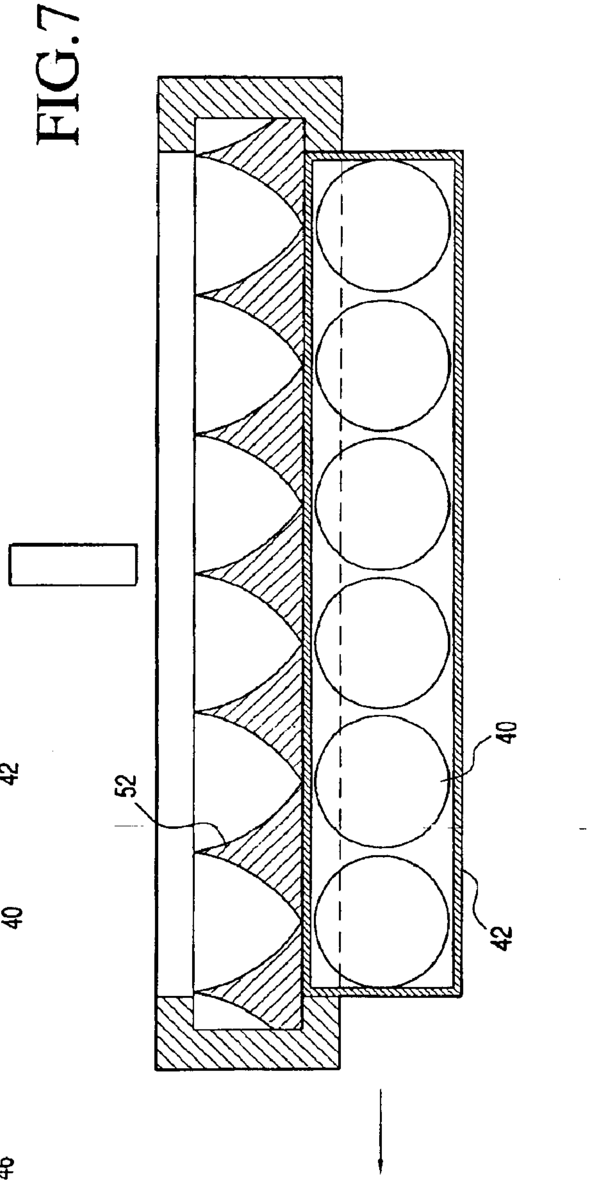
FIG. 7 is a simplified view indicating a prior art system including a modification of the fixture shown in FIG. 6.

FIG. 7 schematically illustrates another embodiment of the system disclosed and claimed in application Ser. No. 09/912,576. In this preferred embodiment, the articles 40 and the box or container 42 may be considered to be respectively equivalent to, or correspond to, the articles 40 and the box or container 42 in FIG. 6. However, fixtures 52 in FIG. 7 are different from the fixtures 44 and 46 in FIG. 6. As will be seen, the fixtures 52 may be considered to be a composite of pairs of fixtures 44 and 46. Specifically, each of the fixtures 52 may be considered to be formed from an aligned pair of one of the fixtures 44 and one of the fixtures 46. The preferred embodiment shown in FIG. 7 is accordingly advantageous because it reduces, by a factor of two (2), the number of fixtures shown in the preferred embodiment of FIG. 6. The concept of the fixtures in FIG. 7 corresponds to the concept of the fixtures 24*a* and 24*b* in FIG. 6.

The embodiments shown in FIGS. 6 and 7 have certain advantages. They allow the articles 16 to be packaged and thereafter boxed before the articles are moved past the radiation source 50. This simplifies the logistics of moving the articles 40 past the radiation source 50. Furthermore, since the articles 40 are boxed before the articles are irradiated, the articles do not have to be individually handled after they have been irradiated. This prevents the articles 40 from being subjected to harmful bacteria after they have been irradiated.

Figure 8:
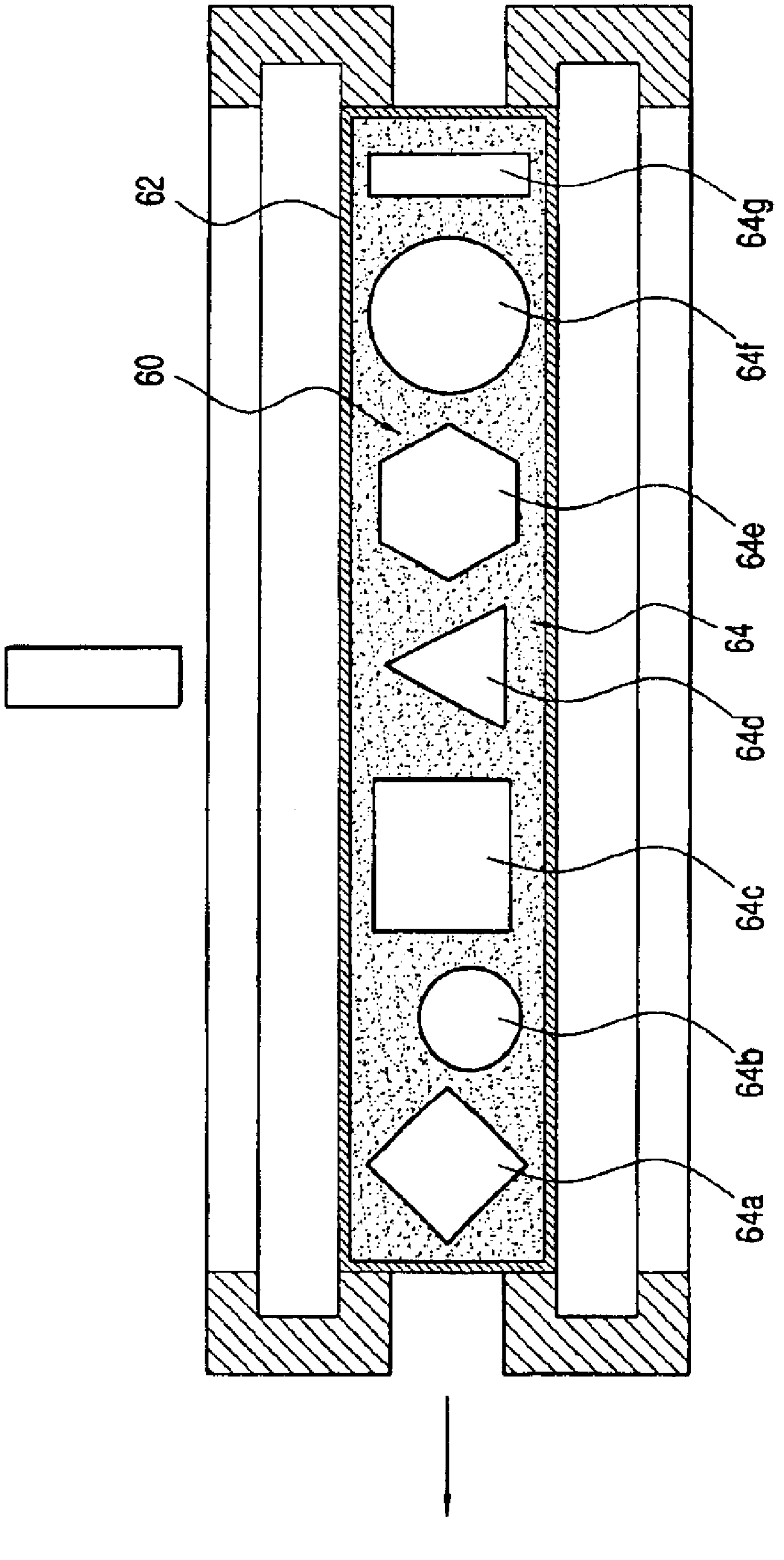
FIG. 8 is a simplified view indicating a preferred embodiment of a system of the invention, in which system articles having irregular characteristics are disposed in a container and in which system a fixture disposed in the container is moved with the container past the radiation source to provide for articles within the container to be irradiated within the particular limits of maximum and minimum dosage at different positions in the articles.

In the embodiments shown in FIGS. 3–5 and in FIGS. 6–7, the fixtures are shown as being disposed outside of the container. In the preferred embodiment of the invention shown in FIG. 8, a fixture generally indicated at 60 is shown as being within a container 62. The fixture 60 may constitute a fluid (e.g. water) which is provided with characteristics to flow into the empty spaces in the container 62.

A plurality of articles generally indicated at 64 may be disposed within the container 62. The articles 64 are specifically illustrated at 64*a*–64*g*. Each of the articles 64*a*–64*g* is shown as having a shape different from the shape of the other articles. The articles 64*c* and 64*g* may have no irregularities. The articles 64*a*, 64*b*, 64*d*, 64*e* and 64*f* may have irregularities. The irregularities in each of the articles 64*a*, 64*b*, 64*d*, 64*e* and 64*f* may be different from the irregularities in each of these other articles.

The fluid fixture 60 may have the same characteristics as the articles 64*a*–64*g*. This causes the characteristics of the combination of the fluid fixture 60 and the articles at any position in a direction indicated by an arrow 66 to be substantially constant. This results from the fact that the fluid fixture 60 fills all of the empty spaces in the container 62 and adapts its position in accordance with the irregularities in the configuration of the articles 64_a_–64_g_. Because of this, the fluid fixture 60 compensates within the container for the irregularities in the characteristics of the articles in the container at the different positions in the articles to provide a uniformity in the radiation dose at the different positions in the articles in the container within particular minimum and maximum limits.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

What is claimed is:

1. A method of irradiating an article from a radiation source where the article absorbs the radiation at different positions in the article in accordance with irregularities in the characteristics of the article at the different positions, including the steps of:

providing the radiation from the source in a particular direction, providing a container with the article disposed in the container, providing in the container a liquid fixture displaceable in the container in accordance with the disposition of the article in the container, moving the container past the radiation from the source in a direction transverse to the particular direction, and absorbing, in the liquid fixture in the container, the radiation energy passing through the container to maintain the absorption of the radiation energy in the article within particular limits.

2. A method as set forth in claim 1 wherein the liquid fixture is provided with characteristics for absorbing the radiation energy at the different positions in the liquid in the container depending upon the irregularities in the characteristics of the articles in the container at the different positions.

3. A method as set forth in claim 2 wherein the articles in the container are moved past the radiation from the source in a direction substantially perpendicular to the particular direction and wherein the articles have at least one of an irregular configuration and density and the liquid fixture has at least one of a configuration and density which, when combined with the at least one of the configuration and density of the articles in the container, provides at least one of a regular configuration and density.

4. A method of irradiating articles from a radiation source where the articles absorb the radiation from the source at different positions in the articles in accordance with irregularities in the characteristics of the articles at the different positions, including the steps of:

providing radiation from the source in a particular direction, providing a container including the articles, moving the articles in the container past the radiation from the source in a second direction transverse to the particular direction, and providing a fixture in the container with characteristics to provide for the absorption of the radiation energy from the source within particular minimum and maximum limits at the different positions in the articles in the container regardless of the characteristics of the articles at the different positions.

5. A method as set forth in claim 4 wherein individual ones of the articles in the container have individual irregularities different from any irregularities of other articles in the container and wherein the fixture in the container is provided with characteristics to provide for the absorption of the radiation energy from the source within particular minimum and maximum limits at the different positions in the articles in the container regardless of the individual irregularities in the individual ones of the articles in the container.

6. A method as set forth in claim 4 wherein the fixture is a liquid having characteristics of filling the space not occupied in the container by the articles in the container.

7. A method as set forth in claim 4 wherein the fixture is water with characteristics of filling the space not 5 occupied in the container by the articles in the container.

8. A method as set forth in claim 4 wherein the fixture within the container is provided with irregularities complementary at the different positions to the irregularities provided by the articles at the different positions.

9. A method as set forth in claim 4 wherein the article is conveyed past the radiation from the source in a direction substantially perpendicular to the particular direction and at a substantially constant speed.

10. A method as set forth in claim 7 wherein the fixture within the container is provided with irregularities complementary at the different positions to the irregularities provided by the articles at the different positions, and the article is conveyed past the radiation from the source in a direction substantially perpendicular to the particular direction and at a substantially constant speed.

11. A method of irradiating articles from a radiation source where the articles absorb the radiation from the source at different positions in the articles in accordance with irregularities in the characteristics of the articles at the different positions, including the steps of providing radiation from the source in a particular direction, providing a container including the articles, moving the articles past the radiation from the source in a second direction substantially perpendicular to the particular direction, and compensating within the container for the irregularities in the characteristics of the articles in the container at the different positions in the articles to provide a uniformity in the radiation dose at the different positions in the articles in the container within particular minimum and maximum limits.

12. A method as set forth in claim 11 wherein the irregularities in the articles in the container at the different positions in the container result from irregularities in at least one of the geometrical configurations of the articles and the densities of the articles in the particular direction in the container and wherein the compensation is provided within the container for the irregularities in the at least one of the dimension of the articles and the densities or the articles in the particular direction in the container.

13. A method as set forth in claim 12 wherein the compensations are provided within the container by a fixture having liquid properties to adjust its position within the container in accordance with the irregularities in the characteristics of the articles within the container.

14. A method as set forth in claim 13 wherein the fixture having the liquid properties is water.

15. A method of irradiating an article from a radiation source where the article has irregular characteristics including at least one of an irregular geometrical shape and an irregular density and absorbs radiation passing through the article by an amount depending upon the irregular characteristics, including the at least one of the irregular geometrical shape and the irregular density, of the article and where the article has different absorption characteristics to radiation at progressive positions in the article, including the steps of:

providing the radiation from the radiation source in a first direction, providing a container including the article inside the container, providing inside the container a liquid fixture having irregular characteristics, including at least one of an irregular geometric shape and an irregular density, at progressive positions to compensate for the differences in the irregularities of the characteristics, including the irregularities in the at least one of the geometric shape and density, of the articles in the container at the progressive positions, disposing the liquid fixture in the container relative to the articles in the container to provide the combination of the articles and the fixture with the compensating characteristics at the progressive positions in response to the radiation, and moving the container at the progressive positions past the radiation source to irradiate the articles in the container at the progressive positions.

16. A method as set forth in claim 15 wherein the fixture has irregular characteristics at progressive positions, depending upon the irregularities in the characteristics of the articles in the container at the progressive positions, to compensate for the irregularities in the characteristics of the articles at the progressive positions.

17. A method as set forth in claim 15 wherein the container is moved past the radiation from the radiation source at a substantially constant speed in a direction substantially perpendicular to the direction of the radiation.

18. A method as set forth in claim 15 wherein the fixture is made from a liquid material having characteristics of absorbing the radiation substantially corresponding to the characteristics of the article in the container in absorbing the radiation.

19. A method of irradiating articles from a radiation source where the articles have characteristics of absorbing at progressive positions different doses of radiation per unit of distance of travel of radiation through the article, including the steps of providing radiation in a particular direction from the source, providing a container including a plurality of articles, providing a fixture having characteristics of absorbing at progressive positions in the fixture different doses of radiation per unit of distance of travel of the radiation through the fixture, the different doses of the radiation per unit of distance of the travel of the radiation through the fixture corresponding to the different doses of the radiation per unit of distance of travel of the radiation through the articles to maintain within particular minimum and maximum limits at the progressive positions the amount of radiation absorbed by the article per unit of travel of the radiation through the articles, disposing the fixture inside the container relative to the articles in the container to maintain within particular limits at the progressive positions the dose of radiation received by the articles per unit of distance of travel of the radiation through the articles, and moving the container at the progressive positions past the radiation from the radiation source to obtain the absorption by the articles of the radiation from the source within the particular limits at the progressive positions in the articles.

20. A method as set forth in claim 19 wherein the container is moved past the radiation from the radiation source at a substantially constant speed in a direction substantially perpendicular to the direction of the radiation from the source.

21. A method as set forth in claim 20 wherein each of the containers is spaced from the adjacent containers by a particular distance within particular limits when the containers are moved past the radiation from the source.

22. A method of irradiating articles from a radiation source where the articles absorb radiation passing through the articles by a dosage depending upon irregularities in the characteristics, including irregularities in the at least one of the geometric shape and density, of the articles and where the articles have different absorption characteristics to radiation at progressive positions in the articles, including the steps of providing the radiation from the radiation source in a first direction, providing a container including the articles, providing a fixture having at the progressive positions characteristics, including at least one of the geometric shape and density, constituting a difference between substantially constant characteristics and the irregularities in the characteristics of the articles in the container at the progressive positions, disposing the fixture inside the container to provide the substantially constant characteristics for the combination of the articles in the container and the fixture in the container at the progressive positions, and moving the container past the radiation from the source at the progressive positions.

23. A method as set forth in claim 22 wherein the container is moved past the radiation from the source in a second direction substantially perpendicular to the first direction.

24. A method as set forth in claim 22 wherein the articles have irregularities in the at least one of the geometrical configuration and the density of the fixture in the first direction at the progressive positions and wherein the fixture has irregularities in the at least one of the geometrical configuration and density of the articles in the first direction at the progressive positions to provide a substantially constant dimension in the first direction at the progressive positions when the at least one of the geometrical configuration and density of the article and the fixture in the first direction at the progressive positions are combined.

25. A method as set forth in claim 22 wherein the progressive positions in the articles in the container and in the fixture in the container are in a direction substantially perpendicular to the first direction.

26. A method of irradiating articles from a radiation source where the articles absorb radiation passing through the articles by a dosage depending upon the characteristics, including the at least one of the geometric shape and the density, of the articles and where the articles have different absorption characteristics to radiation at progressive positions in the articles, including the steps of providing the radiation from the radiation source in a first direction, providing a container including the articles, providing a fixture in the container with characteristics of absorbing the radiation corresponding to the characteristics of the articles to provide a substantially constant absorption in the articles in accordance with a difference between a substantially constant absorption and the absorption of the radiation by the articles at the progressive positions, and moving the container past the radiation from the source in a direction substantially perpendicular to the first direction.

27. A method as set forth in claim 26 wherein the characteristics in the articles include the at least one of the geometrical shape and density of the articles and wherein the characteristics of the fixture in the container include the at least one of the geometrical shape and density of the fixture and wherein the at least one of the geometrical shape and density of the fixture provides the difference between the substantially constant characteristics and the irregularities in the at least one of the geometric shape and density of the articles in the container at the progressive positions.

28. A method as set forth in claim 26 wherein the fixture includes two (2) fixture portions respectively disposed in the container on the opposite sides of the container in the direction of the radiation from the source.

29. A method as set forth in claim 26 wherein the fixture constitutes a liquid fixture having at least one of a geometrical shape and density providing the difference between the substantially constant characteristics and the irregularities in the at least one of the geometrical shape and the density in the articles in the container at the opposite sides of the articles.

30. A method of irradiating articles from a radiation source where the articles absorb radiation by a dosage depending upon the characteristics of the articles and where the articles have different absorption characteristics to the radiation at progressive positions in the articles, the absorption of the radiation in the articles being dependent upon at least one of the geometric shape and density of the articles, including the steps of:

providing the radiation from the source in a particular direction, providing a container including the articles, providing a fixture having a composition with characteristics of absorbing the radiation corresponding to the absorption of the radiation by the at least one of the geometric shape and density of the articles and having at progressive positions absorption characteristics compensating for the absorption characteristics of the articles at the progressive positions, disposing the fixture in the container to provide the at least one of a substantially constant geometric shape and density between the combination of the articles and the fixture at progressive positions in the articles, and moving the combination of the container and the fixture past the radiation from the source in a direction substantially perpendicular to the radiation from the source.

31. A method as set forth in claim 30 wherein the articles are provided with irregularities in at least one of their geometric shape and density and wherein the fixture is provided with irregularities in at least one of its geometric shape and density and wherein the irregularities in at least one of the geometric shape and density of the fixture at the progressive positions are complementary to the irregularities in the at least one of the geometric shape and density of the articles at the progressive positions.

32. In combination, a radiation source for providing radiation in a particular direction, a container including a plurality of articles each having irregularities in its characteristics at different positions in the article where the irregularities in the characteristics produce non-uniformities in the absorption of dosage in the article from the radiation source, a plurality of fixtures inside the container, each of the fixtures having characteristics of absorbing the radiation energy from the source at different positions, relative to the irregularities in the absorption by the articles at the different positions, to provide a substantial uniformity in the absorbed dosage at the different positions in the articles within particular minimum and maximum limits, and a conveyor for moving the container and the articles and the fixtures in the container past the radiation from the source in a direction perpendicular to the particular direction.

33. In a combination as set forth in claim 32 wherein the irregularities in the characteristics of the articles include irregularities in at least one of in the geometrical shape and density of the articles and wherein the irregularities in the characteristics of the fixtures include irregularities in the at least one of the geometrical shape and density of the fixtures.

34. In a combination as set forth in claim 32 wherein the combination of the irregularities in the at least one of the geometrical shape, and density of the articles and in the fixtures provide a substantially constant dosage of the radiation absorbed in the articles within particular minimum and maximum limits.

35. In a combination as set forth in claim 32, the fixture constituting a liquid.

36. In combination, a radiation source for providing radiation in a particular direction, a container including a plurality of articles each having irregularities in its characteristics at different positions in the article where the irregularities in characteristics affect the radiation dosage absorbed by the article at the different positions from the radiation source a plurality of fixtures disposed in the container, each of the fixtures having irregularities in its characteristics to compensate for the irregularities in the characteristics of the articles, and a conveyor for moving the container and the articles and fixtures in the container in a direction substantially perpendicular to the particular direction.

37. In a combination as set forth in claim 36 wherein the irregularities in the characteristics of the articles constitute irregularities in at least one of the geometrical shape and density of the articles and wherein the irregularities in the characteristics of the fixtures constitute irregularities in at least one of the geometrical shape and density of the fixtures.

38. In a combination as set forth in claim 36 wherein the irregularities in the at least one of the geometrical shape and density of the articles constitute irregularities in at least one of the geometrical shape and density of the articles in the direction of the radiation from the source and wherein the irregularities in the at least one of the geometrical shape, and density of the fixtures constitute irregularities in at least one of the geometric shape and density of the fixtures in the direction of the radiation from the source.

39. In a combination as set forth in claim 36 wherein the container and the articles and the fixture in the container are moved past the radiation from the source at a substantially constant speed within particular limits.

40. In a combination as set forth in claim 35 wherein the container is one of a sequence of containers and wherein the fixture is one of a sequence of fixtures and wherein the containers and the fixtures are moved in sequence past the radiation from the source at a substantially constant speed within particular limits and wherein the containers and the fixtures are moved in sequence past the radiation from the source with a minimal separation between the containers within particular limits.

41. In a combination as set forth in claim 36, the fixture constituting water.

42. In combination for receiving radiation in a particular direction from a radiation source, a container including a plurality of articles each having irregularities in its characteristics at different positions in the article where the irregularities in the characteristics of the article cause irregularities to be produced in the dosage absorbed by the article from the radiation source at the different positions, and plurality of fixtures disposed in the container, each of the fixtures having irregularities in its characteristics at different positions in the fixture where the irregularities in the characteristics of the fixture cause irregularities to be produced in the dosage absorbed by the articles from the radiation source at the different positions, the irregularities in the characteristics of the fixture at the different positions complementing the irregularities in the characteristics of the articles at the different positions to provide substantially a uniformity in the dosage absorbed at the different positions in the articles within particular minimum and maximum limits.

43. In a combination as set forth in claim 42, the fixture and the articles being movable with the container past the radiation from the source to receive radiation from the source.

44. In a combination as set forth in claim 42, the fixture constituting a liquid.

45. In a combination as set forth in claim 44, the fixture constituting water.

46. In combination for receiving radiation in a particular direction from a radiation source, a container including a plurality of articles each having irregularities in its characteristics at different positions in the article, and plurality of fixtures disposed in the container, each of the fixtures having irregularities in its characteristics for compensating for the irregularities in the characteristics in the articles in the container at the different positions in the articles to provide substantially a uniformity in the characteristics of the articles at the different positions within particular minimum and maximum limits.

47. In a combination as set forth in claim 46, the container and the articles and the fixtures being disposed relative to the radiation source to provide for the passage of the radiation from the source through the articles in the container and the fixtures in the container.

48. In a combination as set forth in claim 47, the irregularities in the characteristics of the articles constituting at least irregularities in at least one of the geometrical shape and density of the articles and the irregularities in the characteristics of the fixture constituting irregularities in the at least one of the geometrical shape and density of the fixture.

49. In a combination as set forth in claim 47, the fixtures in the container constituting a liquid.

50. In combination, a container, a plurality of articles disposed in the container for irradiation, each of the articles having irregularities in its characteristics at progressive positions in the articles in response to radiation, and a fixture disposed in the container and having irregularities in its characteristics at progressive positions in response to radiation to compensate for the irregularities in the characteristics of the articles in the container at the progressive positions.

51. In a combination as set forth in claim 50 wherein the irregularities in the characteristics of the articles and in the fixtures provide irregularities in the absorption in the articles and the fixtures of radiation.

52. In a combination as set forth in claim 50, a conveyor for moving the container and the fixture in a first direction, and a source of radiation disposed relative to the container and the articles and the fixtures for irradiating the articles and the fixtures in the container in a second direction substantially perpendicular to the first direction.

53. In a combination as set forth in claim 50 wherein the fixtures constitute a liquid having substantially the same characteristics per unit of distance of absorbing irradiation as the articles in the container.

54. In a combination as set forth in claim 53 wherein the irregularities in the characteristics of the articles and in the fixtures provide irregularities in the absorption of radiation by the articles and the fixtures.

55. In a combination as set forth in claim 50, a conveyor for moving the container and the fixture in a first direction, and a source of radiation disposed relative to the container and the articles and the fixtures for irradiating the articles and the fixtures in the container in a second direction substantially perpendicular to the first direction.

56. In a combination as set forth in claim 53 wherein the fixtures constitute water.

* * * * *